United States Patent [19]

Saggers

[11] Patent Number: 4,753,242

[45] Date of Patent: Jun. 28, 1988

[54] SKULL HELMET FOR CIRCULATING COOLING FLUID

[76] Inventor: Michael J. Saggers, 9 Pennycroft, Harpenden, Herts., United Kingdom

[21] Appl. No.: 820,635

[22] Filed: Jan. 21, 1986

[30] Foreign Application Priority Data

Jan. 28, 1985 [GB] United Kingdom ................ 8502016

[51] Int. Cl.⁴ ................................................ A61F 7/10
[52] U.S. Cl. ................................. 128/380; 62/259.3; 128/400; 165/46
[58] Field of Search ............... 128/380, 400; 62/259.3, 62/261; 165/46

[56] References Cited

U.S. PATENT DOCUMENTS

| | | | |
|---|---|---|---|
| 2,116,009 | 5/1938 | Brown | 128/403 X |
| 3,463,161 | 8/1969 | Andrassy | 165/46 X |
| 4,331,151 | 5/1982 | Golden | 128/400 X |
| 4,566,455 | 1/1986 | Kramer | 128/380 |

FOREIGN PATENT DOCUMENTS

| | | | |
|---|---|---|---|
| 278767 | 2/1952 | Switzerland | 128/400 |
| 446788 | 5/1936 | United Kingdom | 128/380 |

*Primary Examiner*—Anton O. Oechsle
*Attorney, Agent, or Firm*—Banner, Birch, McKie & Beckett

[57] ABSTRACT

This invention relates to a skull helmet, which in use, is worn on the head of a patient and receive circulatory cooling fluid to cool the patient's scalp. The helmet is particularly useful when a patient undergoes chemotherapy in that the cooling effect has been found to minimize hair loss in some applications and the term heat transfer fluid as used herein shall apply to both coolants and heating fluids.

9 Claims, 2 Drawing Sheets

SKULL HELMET FOR CIRCULATING COOLING FLUID

This invention relates to a skull helmet which, in use, is worn on the head of a patient and receives circulatory cooling fluid to cool the patient's scalp. The helmet is particularly useful for a patient who undergoes chemotherapy treatment in that the cooling effect has been found to minimize hair loss. However, it is envisaged that the helmet may receive a heating fluid in some applications and the term heat transfer fluid as used herein shall apply to both coolants and heating fluids.

The invention provides a skull helmet comprising a plurality of compartments through each of which a heat transfer fluid can pass from an inlet at one end of the compartment to an outlet at the opposite end of the compartment and wherein a fluid distribution manifold is provided adjacent said inlet end of the compartments, the manifold having a fluid inlet to receive circulatory fluid from a source and a fluid outlet connected to the inlet of each of said compartments to supply heat transfer fluid thereto.

According to a feature of the invention a baffle may be provided in the manifold between said manifold inlet and the manifold outlets so as to encourage even distribution of fluid to the outlets.

According to another feature of the invention, the manifold may comprise a substantially cylindrical chamber and wherein said manifold inlet and outlets comprise passageways arranged radially with respect to the axis of the chamber. In constructions where this feature is adopted, the chamber may be formed from a pair of similar dished parts which are assembled in face to face relationship.

According to yet another feature of the invention, the manifold may include means adapted to receive a chinstrap for the helmet. In constructions where this feature is adopted said means may comprise a bracket extending from the manifold chamber remote from said manifold outlets.

According to a still further feature of the invention, an additional fluid distribution manifold as defined in any of the four immediately preceding paragraphs is provided at the outlet end of said compartments, but in which said manifold outlets are connected to receive heat transfer fluid from the compartments and said manifold inlet returns the heat transfer fluid to source.

Preferably, the compartments are formed from a flexible non-porous sheet material and in which each compartment comprises a pair of sheet panels connected together around their peripheries in superposed relationship the panels being further connected together at a multiplicity of discrete locations so as to produce a tortuous flow path between the panels through which the heat transfer fluid is to flow.

An embodiment of the invention will now be described, by way of example, with reference to the accompanying drawings, in which.

Figure 1:
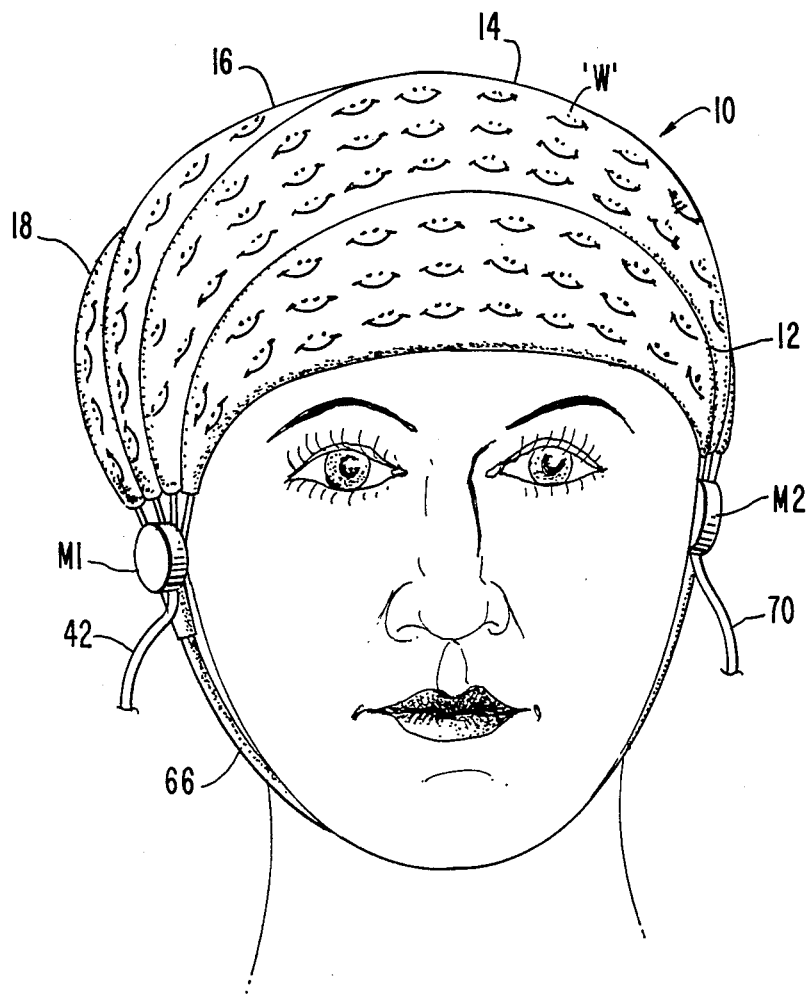
FIG. 1 is a general perspective view of a skull helmet according to the invention.

Referring to the drawings, a skull helmet 10 comprises a series of segmental compartments 12, 14, 16 and 18 attached one end to the next to form the helmet which can be donned by a patient. Each compartment e.g. compartment 12 comprises an inner panel 12a and an outer panel 12b both formed from a woven nylon material, having a polyeurathane coating which are high-frequency welded together around their peripheries. An inlet pipe 20 is interposed between the inner and outer panels and extends from one end of the compartment and similarly an outlet pipe 22 extends from the opposite end of the compartment. The inner and outer panels are further welded together at a multiplicity of discrete locations by means of annular weld zones 'W' thereby producing a tortuous flow path between the panels through which the heat transfer fluid is to flow. It will be appreciated that this arrangement enhances the heat transfer characteristics of the compartments.

The compartments are connected one to the next as by stiching to form the helmet so that all the inlet pipes are present at one side of the helmet and are connected to an inlet manifold M1 and all the outlet pipes are present at the opposite side of the helmet and are connected to an outlet manifold M2.

Figure 2:
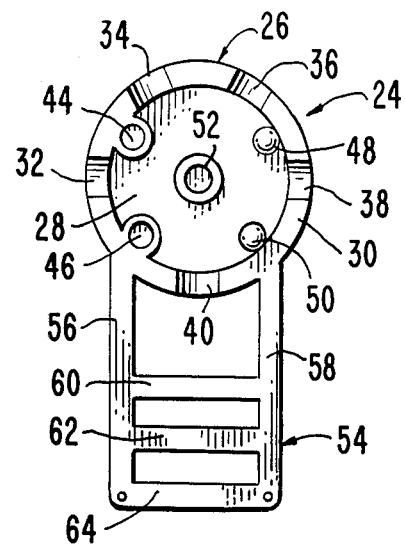
FIG. 2 is a cross-sectional view of the manifold.
Figure 3:
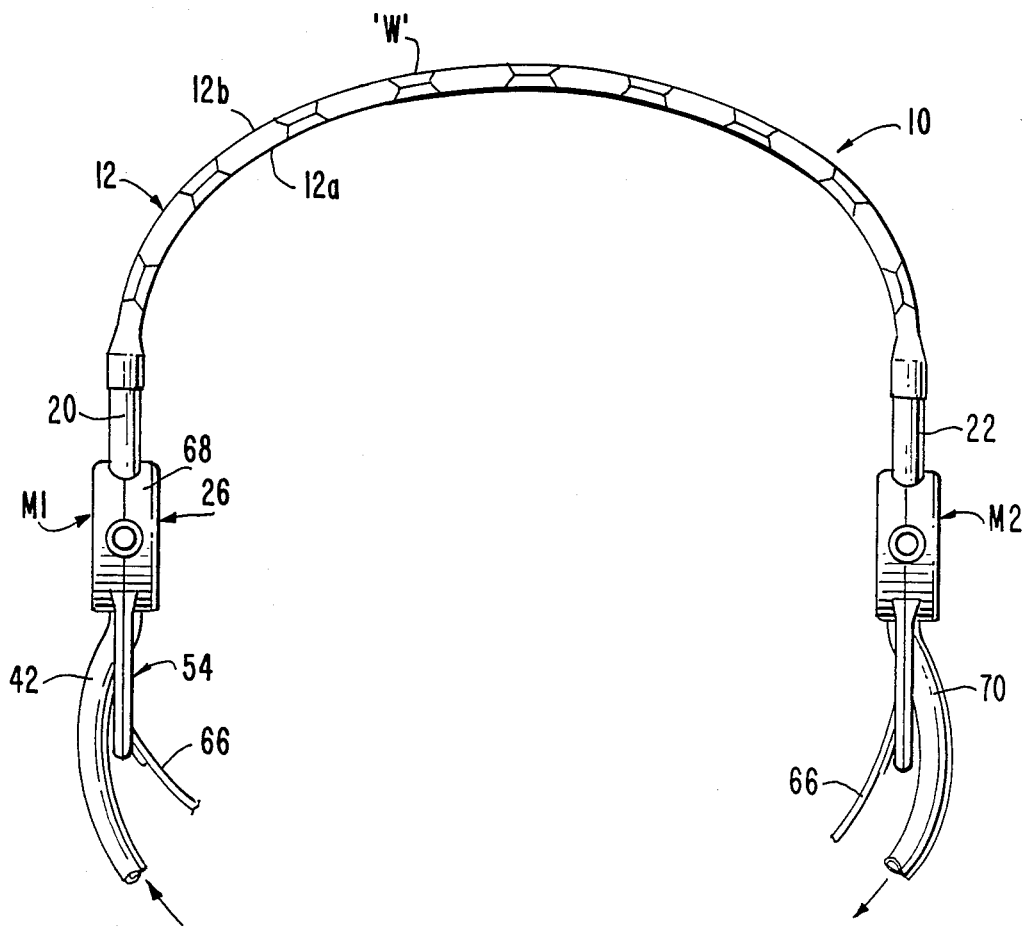
FIG. 3 is an end view of the skull helmet shown in FIG. 1 with one compartment shown in cross-section.

The inlet and outlet manifolds are of like construction and comprise a pair of moulded components which are mirror images of one another. One such manifold component 24 is illustrated in FIG. 2. The component comprises a dished part 26 defined by a base 28 and an integral annular wall 30. The annular wall is formed with four equi-distant arcuate recesses 32, 34, 36 and 38, respectively which together with similar recesses of the mating component provide the manifold outlets. The outlets receive the projecting ends of the inlet pipes. The annular wall is further formed with arcuate recess 40 which together with a similar recess of the mating component provides the manifold inlet which receives a feed hose 42 to supply heat transfer fluid to the manifold. A pair of hollow locating sockets 44 and 46 and a pair of locating pins 48 and 50 are upstanding from the base 28 and receive the corresponding pins and sockets respectively of the mating manifold component when the components are brought together to form the manifold.

A central peg 52 is upstanding from base 28 which together with a similar peg of the mating component provides a cylindrical baffle internally of the manifold.

A bracket 54 depends from the dished part 26 remote from the manifold outlets and comprises parallel legs 56 and 58, one on each side of manifold inlet 40, interconnected by spaced transverse bars 60, 62 and 64 which provide attachment means for a chin strap 66. When the manifold components are secured together, the dished parts form a cylindrical chamber 68 from which the inlet and outlet pipes extend radially with respect to the axis of the chamber.

An outlet hose 70 connected to the outlet manifold M2 returns the heat transfer fluid to source.

I claim:

1. A skull helmet for controlling scalp temperature by means of a circulatory heat transfer fluid passed through said helmet, the helmet comprising a plurality of compartments formed from a flexible non-porous sheet material, each compartment comprising a pair of sheet panels, said panels being welded together around their peripheries in superposed relationship and welded together at a multiplicity of discrete locations so as to produce a tortuous flow path between said panels through which the heat transfer fluid is to flow, each compartment having a compartment inlet at one end thereof and a compartment outlet at an opposite end thereof, said compartments being connected one to the next to form said helmet so that all of said compartment inlets are located at one side of the helmet and all of said compartment outlets are located at the opposite side of the helmet, an inlet fluid distribution manifold having a first fluid inlet to receive the circulatory fluid from a source and a plurality of first fluid outlets, each of said first fluid outlets being connected to a respective one of said compartment inlets to supply said circulatory fluid to each compartment, and an outlet fluid distribution manifold having a plurality of second fluid inlets and a second fluid outlet, each of said second fluid inlets being connected to a respective one of said compartment outlets to receive the circulatory fluid from each compartment and to return the circulatory fluid to the source through said second fluid outlet.

2. A skull helmet according to claim 1 wherein a baffle is provided in the inlet fluid distribution manifold between said first fluid inlet and said first fluid outlets so as to encourage even distribution of said fluid to the first fluid outlets.

3. A skull helmet according to claim 1 or claim 2, wherein the inlet fluid distribution manifold comprises a substantially cylindrical chamber and said first fluid inlet and outlets comprise passageways arranged radially with respect to the axis of the chamber.

4. A skull helmet according to claim 3,
wherein said cylindrical chamber is formed from a pair of similar dished parts which are assembled in a face to face relationship.

5. A skull helmet according to claim 1,
wherein said manifolds include means adapted to receive a chin-strap for the helmet.

6. A skull helmet according to claim 5,
wherein said means comprises a bracket extending from the manifold at a location remote from said first fluid outlets in said inlet fluid distribution manifold and remote from said second fluid inlets in said outlet fluid distribution manifold.

7. A skull helmet according to claim 1 or 2 wherein a baffle is provided in the outlet fluid distribution manifold between said second fluid inlets and said second fluid outlet.

8. A skull helmet according to claim 7 wherein the outlet fluid distribution manifold and said second fluid inlets and outlet comprise passageways arranged radially with respect to the axis of the chamber.

9. A skull helmet according to claim 8 wherein said cylindrical chamber is formed from a pair of similar dished parts which are assembled in a face to face relationship.

* * * * *